United States Patent
Cramail et al.

(10) Patent No.: US 8,835,692 B2
(45) Date of Patent: Sep. 16, 2014

(54) METHOD FOR PREPARING POLYOLS BY MEANS OF THIOLATION AND PRODUCTS SUCH AS THOSE OBTAINED

(75) Inventors: Henri Cramail, Sainte Terre (FR); Aurelie Boyer, Bordeaux (FR); Eric Cloutet, Saint Caprais de Bordeaux (FR); Carine Alfos, Pessac (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 363 days.

(21) Appl. No.: 13/501,802

(22) PCT Filed: Oct. 13, 2010

(86) PCT No.: PCT/FR2010/052171
§ 371 (c)(1),
(2), (4) Date: Jul. 12, 2012

(87) PCT Pub. No.: WO2011/045536
PCT Pub. Date: Apr. 21, 2011

(65) Prior Publication Data
US 2012/0283467 A1  Nov. 8, 2012

(30) Foreign Application Priority Data
Oct. 13, 2009 (FR) .................................... 09 57146

(51) Int. Cl.
*C07C 319/00* (2006.01)
*C07C 321/00* (2006.01)
*C07C 323/00* (2006.01)
*C07C 381/00* (2006.01)
*C07C 323/52* (2006.01)
*C08G 18/38* (2006.01)

(52) U.S. Cl.
CPC .......... *C07C 323/52* (2013.01); *C08G 18/3865* (2013.01)
USPC ........................................................ 568/43

(58) Field of Classification Search
None
See application file for complete search history.

(56) References Cited

U.S. PATENT DOCUMENTS

| 3,328,430 A | 6/1967 | Hansen et al. |
| 4,647,678 A | 3/1987 | Eckwert et al. |
| 5,026,881 A | 6/1991 | Gruber |
| 5,380,886 A | 1/1995 | Daute et al. |
| 6,107,433 A | 8/2000 | Petrovic et al. |
| 2005/0154221 A1 | 7/2005 | Lysenko et al. |
| 2007/0232816 A1 | 10/2007 | Soi et al. |

FOREIGN PATENT DOCUMENTS

| WO | 2006094227 A2 | 9/2006 |
| WO | 2007143135 A2 | 12/2007 |

OTHER PUBLICATIONS

Buess et al., "Addition of Mercaptoacetic Acid to Terpenes and Related Compounds", Journal of Organic Chemistry, vol. 22, No. 2, Feb. 1957, pp. 197-200, XP002585110.
Weber et al., "Antioxidants eliminate stereomutation and thioether formation during lipase-catalysed thioesterification and transthioesterification for the preparation of uniform cis- and trans-unsaturated thioesters", Chemistry and Physics of Lipids, vol. 105, No. 2, Apr. 2000, pp. 215-223, XP002585111.
Croston et al., "Polymerization of Drying Oils. VI. Catalytic Polymerization of Fatty Acids and Esters With Boron Trifluoride and Hydrogen Fluoride", The Journal of the American Oil Chemists' Society, Aug. 1952, pp. 331-333.
Findley et al., "Expoxidation of Unsaturated Fatty Materials with Peracetic Acid in Glacial Acetic Acid Solution", Eastern Regional Research Laboratory, vol. 67, pp. 412-414, 1944.
Guo et al., "Structure and Properties of Halogenated and Nonhalogenated Soy-Based Polyols", Kansas Polymer Research Center, Pittsburg State University, Aug. 7, 2000, pp. 3900-3910.
Guo et al., "Polyols and Polyurethanes from Hydroformylation of Soybean Oil", Journal of Polymer and the Environment, vol. 10, Nos. 1/2, Apr. 2002, pp. 49-52.
Petrovic et al., "Epoxidation of soybean oil in toluene with peroxoacetic and peroxoformic acids—kinetics and side reactions", Eur. J. Lipid Sci. Technol., vol. 104, 2002, pp. 293-299.
Refvik et al., "Ruthenium-Catalyzed Metathesis of Vegetable Oils", JAOCS, vol. 76, No. 1, 1999, pp. 93-98.
Sinadinovic-Fiser et al., "Kinetics of in situ Epoxidation of Soybean Oil in Bulk Catalyzed by Ion Exchange Resin", JAOCS, vol. 78, No. 7, 2001, pp. 725-731.
Teng et al., "Spectroscopic investigation of the blowing process of soyabean oil", Surface Coating International Part 8: Coatings Transactions, vol. 86, pp. 221-229, Sep. 2003.
Schaeffer et al., "Formation of Isomeric Hydrox Acids by Sulfation of Oleic Acid", Eastern Regional Research Laboratory, vol. 66, Nov. 1944, pp. 1924-1925.
Vlcek et al., "Optimization of the Chemoenzymatic Epoxidation of Soybean Oil", JAOCS, vol. 83, No. 3, 2006, pp. 247-252.
International Search Report dated Feb. 3, 2011, from corresponding PCT application.

*Primary Examiner* — Clinton Brooks
(74) *Attorney, Agent, or Firm* — Young & Thompson

(57) ABSTRACT

A method for preparing a polyol having the following general formula (I): the method including a step of transesterification followed by a step of thiolation. The present invention also relates to polyols with the formula (T) such as those defined above.

24 Claims, No Drawings

METHOD FOR PREPARING POLYOLS BY MEANS OF THIOLATION AND PRODUCTS SUCH AS THOSE OBTAINED

The present invention relates to a novel method for preparing polyols, diols in particular, and to the novel polyols such as obtained.

Different approaches exist for synthesizing polymers from vegetable oils. The first, the most widespread, consists of considering triglycerides as base materials, these able to be epoxidized then alcoholized or hydroformylated for example so that they can be made functional and polymerisable.

Oils are a mixture of triglycerides (triesters) formed by condensation of fatty acids and glycerol. The high number of types of fatty acids (up to 24) present in each fat and the multiple possibilities of their combinations with the molecules of glycerol mean that fats are very complex mixtures of compounds whose properties vary from one type of oil to another. The nature of the triglycerides may therefore vary within one same oil.

The reaction sites present in a triglyceride are chiefly double bonds and ester functions. The reactivity of the double bonds allows the introduction of hydroxyl functions, thereby providing access to pluri-hydroxylated monomers. It is nonetheless impossible to obtain triglycerides having perfectly defined structures and functionalities.

The synthesis of polyols derived from vegetable oil is well described in the literature since these form excellent precursors for the synthesis of polymers. These materials are gaining increasing popularity on account of the natural origin of the precursors and the attractive properties contributed by the structure and the composition of vegetable oils. The reaction sites in all fats are the ester functions and double bonds. Some oils also have other groups such as hydroxyls or epoxides.

The double bonds of these compounds are generally not sufficiently reactive to act as radical polymerization sites. Nevertheless, at high temperature (330° C.), the double bonds may migrate along the backbone to form conjugate sites which facilitates condensations of Diels-Alder type. Some oligomers have been synthesized by vulcanization of oils with sulfur monochloride and used as additives in the gum industry for example. Some oligomers have also been synthesized by cationic polymerization in the presence of boron trifluoride (Croston et al., *J. Amer. Oil Chem. Soc.* 1952, 331-333), for applications in ink formulations. Other reactions involving double bonds such as polymerization by metathesis have allowed oligomers to be obtained (Refyik et al., *J. Amer. Oil Chem. Soc.* 1999, 76, 93-98) and the materials derived therefrom can rarely be given use since they are very ill-defined.

It is therefore necessary to better control the functionalization of vegetable oils.

As already indicated, the presence of double bonds on the backbone allows the inserting of hydroxyl groups. This insertion can be obtained by direct oxidation of the double bonds which consists of passing a stream of oxygen through the oil heated to 135° C. (G., Soucek et al. "Spectroscopic investigation of blowing process of soybean oil", Surface Coatings International, Part B, Coatings Transactions. 2003, 86: 221-229). The controlling of oxidation is unsatisfactory and numerous by-products are formed such as peroxides, aldehydes, ketones, chain scission, etc. The only advantage of these polyols is their low cost price and their one-step synthesis, despite numerous treatments applied to the end product (odours, high acid number, dark colour, etc.).

An organometallic catalyst can also be used to better control the oxidation reaction (WO2006/094227; WO2007/143135) in the presence of an oxidant.

Polyols having primary hydroxyls can be prepared by hydroformylation of the unsaturations (Guo et al., J. of Polymers and the Environment. 2002, 10: 49-52). This process entails a reaction between carbon monoxide and dihydrogen, leading to the formation of an aldehyde group which is converted to a hydroxyl by hydrogenation. The rhodium-based catalysts generally used are highly efficient (conversions close to 100%) but also very costly. Conversely, cobalt-based catalysts are low-cost but less efficient. Ozonolysis of the double bonds also allows polyols to be obtained having terminal hydroxyl groups (Guo et al., J. of Polymer Sci., 2000, 38: 3900-3910). The ozone is passed through a solution of vegetable oil and ethylene glycol in the presence of an alkaline catalyst.

Another access route to polyols is to conduct a prior epoxidation reaction of the unsaturations. Numerous studies in the literature describe the epoxidation of fats (Swern, et al., J. Am. Chem. Soc. 1944, 66, 1925-1927; Findley et al., J. Am. Chem. Soc. 1945, 67, 412-414; U.S. Pat. Nos. 5,026,881; 3,328,430; Petrovic' et al., Eur. J. Lipid Sci. Technol. 2002, 104: 293-299 and U.S. Pat. No. 4,647,678). Petrovic recently showed that it is possible to achieve epoxidation of vegetable oil by enzymatic route (Vlcvek, T. et al., J. Amer. Oil Chem. Soc. 2006, 83: 247-252) or catalysed by an ion exchange resin (Sinadinovic'-Fiser et al., J. Amer. Oil Chem. Soc. 2001, 78: 725). Nevertheless, the most frequent route is the use of a peracid formed in situ, generally hydrogen peroxide in the presence of a carboxylic acid (most often formic acid in catalytic quantity). The reaction is conducted at between 50° C. and 80° C. for 1 to 4 hours.

It is the objective of the present invention to provide a method for preparing polyols from esters of vegetable oil with which it is possible to overcome the aforementioned disadvantages.

Another objective of the present invention is to provide a method which, contrary to the prior art methods which concern chemical conversion from triglycerides having ill-defined structures, consists of a simple efficient route for chemical modification of monoesters or triglycerides to obtain functional precursors having controlled functionality.

A further objective of the present invention is to provide a simple two-step preparation method via mono-or diesters of vegetable oil.

One objective of the present invention is to provide a two-step method providing access to novel synthons, mono-esters or di-esters, these all being at least bi-functional (polyols) and having well defined structures.

One objective of the present invention is to provide a method for preparing polyols having primary hydroxyl functions.

The present invention concerns a method for preparing a polyol meeting the following general formula (I'):

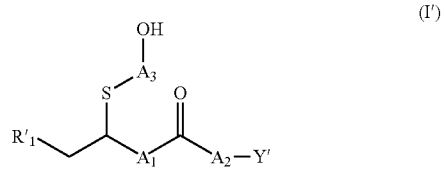

where:

R'$_1$ is a straight-chain or branched alkyl group comprising 1 to 14 carbon atoms, the said alkyl group optionally containing one or two side substituents —S-A$_3$-OH, $A_1$ is a divalent alkylene radical, straight-chain or branched, comprising 2 to 14 carbon atoms, $A_2$ is a —O-$A_4$-O— radical, $A_4$ representing a divalent alkylene radical, straight-chain or branched, comprising 1 to 20 carbon atoms, preferably 1 to 10 carbon atoms, optionally comprising one or more substituents chosen in particular from the group formed of the phenylene radical and the radical of formula —(CH$_2$OCH$_2$)$_n$—, n representing an integer of 1 to 100, preferably 6 to 50, and is preferably 6, 13 or 45, or $A_2$ is a radical of formula —(OCH$_2$CH$_2$)$_n$—O—, n being such as defined above, $A_4$ preferably representing a radical of formula —CH$_2$-A'$_3$-CH$_2$—, A'$_3$ representing a group of formula —(CH$_2$OCH$_2$)$_n$—, n representing an integer of between 1 to 100, preferably 6 to 50, and is preferably 6, 13 or 45, or a phenylene radical, $A_3$ is a divalent alkylene radical, straight-chain or branched, comprising 1 to 10 carbon atoms, optionally substituted, Y' is a hydrogen atom or a group of formula (A')

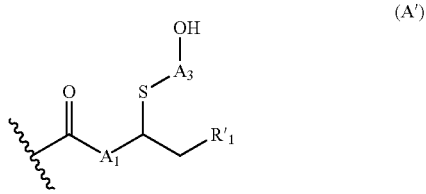

$A_1$, $A_3$ and R'$_1$ being such as defined above in formula (I'), the said method comprising the following steps:

a) a transesterification step of a compound of the following formula (II'):

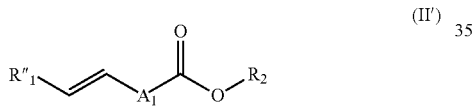

$A_1$ being such as defined above in formula (I'),

R"$_1$ representing a straight-chain or branched alkyl group comprising 1 to 14 carbon atoms, the said alkyl group optionally containing one or two double bonds, and R$_2$ representing a straight-chain or branched alkyl group comprising 1 to 10, preferably 1 to 6 carbon atoms, with a diol of the following formula (III):H-$A_2$-H (III)

$A_2$ being such as defined above in formula (I'), to obtain a compound of the following formula (IV'):

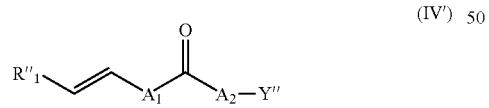

$A_1$, $A_2$ and R"$_1$ being such as defined above, and

Y" representing a hydrogen atom or a group of formula (A")

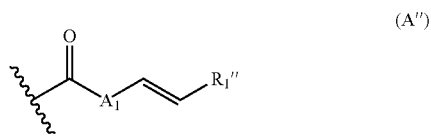

$A_1$ and R"$_1$ being such as defined above, b) a thiolation step of the above-mentioned formula (IV') to obtain a compound of formula (I') such as defined above, the thiolation step being a reaction step of the compound of above-mentioned formula (IV') with a thiol of formula HS-$A_3$-OH, $A_3$ being such as defined above in formula (I'), and c) a step to collect the compound of formula (I') such as defined above.

Therefore, the method of the invention consists of synthesizing novel polymers from mono-esters of fatty acids. The latter are generally obtained by transesterification of triglycerides for example with a short-chain alcohol (R$_2$OH, R$_2$ being such as defined above) preferably with methanol or ethanol.

These esters and more particularly the methyl or ethyl esters of sunflower or castor oil were therefore used as basic 'synthons' in the present invention.

Using a variety of sunflower oil whose oleic acid content is particularly high, and by separating the different methyl esters of the sunflower oil by fractional distillations, methyl esters of oleic acid are obtained (only one double bond per fatty chain) of high purity. It is starting from this monofunctional precursor that it is then possible to provide a chosen number of hydroxyl groups and thereby to control the functionality of this 'synthon' monomer. A well-defined structure of such monomers is effectively essential for preparing polymer materials having controlled, reproducible properties. Since the desired polymers are straight-chain, it was sought for example to create monomers that are at least difunctional (di-OH) from methyl esters of oleic sunflower.

The different reactions involved for the method of the present invention are (i) transesterification of the ester group by diols allowing the grafting of a first primary hydroxyl function (above-mentioned step a), and (ii) a thiolation step allowing the grafting of a second primary hydroxyl function via a thiol function (above-mentioned step b).

Therefore, with the present invention it is possible to prepare diols meeting one of the two following formulas:

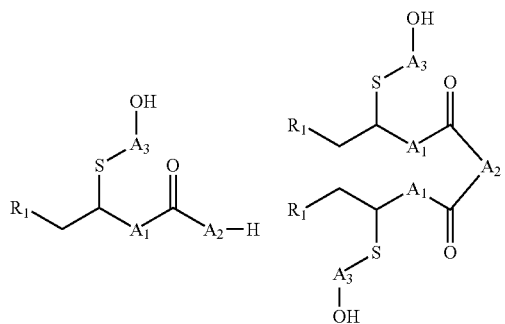

i.e. firstly non-symmetric diols with two primary OH functions, and secondly symmetric diols with two primary OH functions.

According to the present invention, the "alkyl" radicals represent saturated hydrocarbon radicals, straight-chain or branched, comprising 1 to 14 and preferably 1 to 10 carbon atoms, more preferably 1 to 5 carbon atoms (they may typically be represented by the formula $C_nH_{2n+1}$, n representing the number of carbon atoms). Particular mention can be made, when they are straight-chain, of the methyl, ethyl, propyl, butyl, pentyl, hexyl, octyl, nonyl and decyl radicals. When they are branched or substituted by one or more alkyl radicals, particular mention can be made of the isopropyl, tert-butyl, 2-ethylhexyl, 2-methylbutyl, 2-methylpentyl, 1-methylpentyl and 3-methylheptyl radicals.

According to the present invention, the "alkylene" radicals represent radicals (also called alkylidenes) derived from alkanes whose two terminal hydrogen atoms have been removed. When the said alkylene radicals are straight-chain, they can be represented by the formula —(CH$_2$)$_m$—, m corresponding to the number of carbon atoms of the alkane from which the alkylene radical is derived.

According to another embodiment, the present invention concerns a method for preparing a diol meeting the following general formula (I):

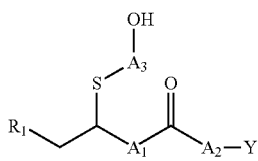
(I)

where:
R₁ is a straight-chain or branched alkyl group comprising 1 to 14 carbon atoms,
A₁, A₂ and A₃ are such as defined above in formula (I'), and
Y is a hydrogen atom or a group of formula (A)

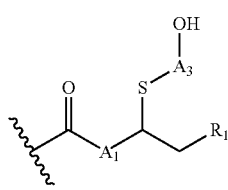
(A)

A₁, A₃ and R₁ being such as defined above,
the said method comprising the following steps:
a) a transesterification step of a compound of following formula (II):

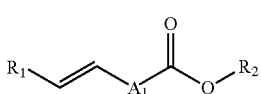
(II)

R₁ being such as defined above,
R₂ and A₁ being such as defined above in formula (I'), with a diol of following formula (III):H-A₂-H   (III)

to obtain a compound of following formula (IV):

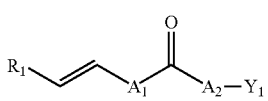
(IV)

A₁, A₂ and R₁ being such as defined above in formula (I),
Y₁ representing a hydrogen atom or a group of formula (A₁)

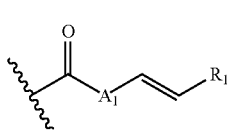
(A₁)

A₁ and R₁ being such as defined above,
b) a thiolation step of the compound of above-mentioned formula (IV) to obtain a compound of formula (I) such as defined above, and
c) a step to collect the compound of formula (I) such as defined above.

The present invention also concerns a method such as defined above for preparing a diol of the following formula (I-1):

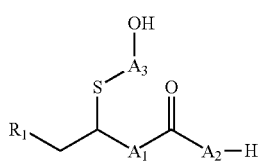
(I-1)

A₁, A₂, A₃ and R₁ being such as defined in formulas (I) and (I').

The compounds of formula (I-1) are formula (I) compounds in which Y is a hydrogen atom. This diol comprises two primary hydroxyl functions'.

The present invention also concerns a method such as defined above for preparing a diol of the following formula (I-2):

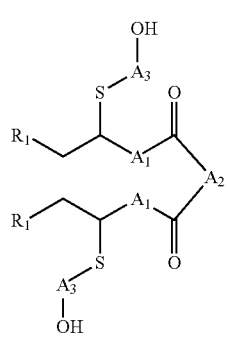
(I-2)

A₁, A₂, A₃ and R₁ being such as defined in formulas (I) and (I').

The compounds of formula (I-2) are formula (I) compounds in which Y is a group of formula (A) such as defined above. This diol comprises two primary hydroxyl functions.

Preferably, step a) is conducted in the presence of a catalyst chosen from the group formed of magnesium oxide, zinc acetate and sodium methanolate.

Preferably, step a) of the method of the invention is conducted at a temperature of between 150 and 200° C. under a stream of nitrogen.

According to one preferred embodiment, this step a) such as defined above is performed without a solvent, which is ecologically most advantageous.

The present invention also concerns a method for preparing a diol such as defined above, characterized in that the product of formula (IV) obtained after step a) is in the form of a mixture of monoesters and diesters, the monoesters meeting the following formula (IV-1):

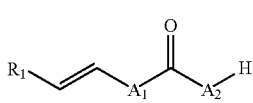
(IV-1)

and the diesters meeting the following formula (IV-2):

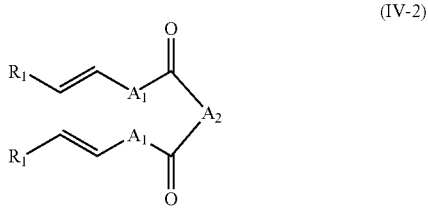

(IV-2)

$A_1$, $A_2$ and $R_1$ being such as defined in formula (I).

The monoester of formula (IV-1) corresponds to a compound of formula (IV) in which $Y_1$ is H and the diester of formula (IV-2) corresponds to a compound of formula (IV) in which $Y_1$ is a group of formula ($A_1$).

According to one preferred embodiment, the thiolation step of the preparation method such as defined above is a radical addition reaction in the presence of a radical initiator, azobisisobutyronitrile (AIBN) in particular.

The thiolation step according to the present invention consists of causing the compound obtained after step a) to react with a thiol of formula HS-$A_3$-OH, $A_3$ being such as defined above.

Preferably, the thiolation step b) of the method according to the invention is conducted in the presence of toluene at a temperature of between 60° C. and 80° C., and preferably at 70° C.

According to one particularly preferred embodiment, step b) consists of causing the compound of formula (IV) (or (IV')) to react with 2-mercaptoethanol (compound HS-$A_3$-OH where $A_3$ is a radical $C_2H_4$).

Detailed Description of the Steps of the Method

1. Step a): Transesterification Reaction of the Compounds of Formula (II') or (II)

For the present invention, this transesterification is preferably performed from the ester of a light alcohol (in particular methanol or ethanol . . . ) of oleic sunflower (compound of formula (II) or (II')) and from a diol (compound of formula (III)) in the presence of magnesium oxide in particular as catalyst. Several syntheses are conducted with different diols to modulate the properties of the monomers and hence of the resulting polymers. Transesterifications were therefore performed from propanediol, hexanediol, butanediol and hydroxytelechelic polyethylene oxide).

The reaction is conducted at between 150° C. and 200° C. under a stream of nitrogen. The progress of the reaction is monitored by different analyses, NMR in particular (disappearance of the singlet of the methyl group). Depending on the reaction conditions, two products are obtained.

If the diol used is placed in large excess, a majority of at least 80% even 95% of monoesters (or derivatives of monoglycerides) is obtained having a terminal hydroxyl group. This alcohol at the end of the chain then imparts the monomer with a first functionality.

Conversely, if a shortfall of the diol is deliberately added, a majority of at least 60% even 85% of diesters is obtained (or derivatives of digycerides). This second precursor then has exactly two double bonds via which the hydroxyl groups will be introduced giving access to monomers having two functionalities.

| Alcohols used | Reaction time | | Yield | |
|---|---|---|---|---|
| | Synthesis of monoesters | Synthesis of diesters | Synthesis of monoesters | Synthesis of diesters |
| Propanediol | 10 h | 15 h | 80% | 62% |
| Hexanediol | 10 h | 15 h | 80% | 60% |
| Poly(ethylene oxide) ($M_w$ = 300 g/mol) | 15 h | 20 h | 75% | 59% |
| Poly(ethylene oxide) ($M_w$ = 600 g/mol) | 15 h | 20 h | 75% | 59% |

Step a) (where $R_1$=$C_6H_{13}$; $A_1$=$C_9H_{18}$; $R_2$=$CH_3$, $A_2$=ORO) can in particular be represented by the following scheme:

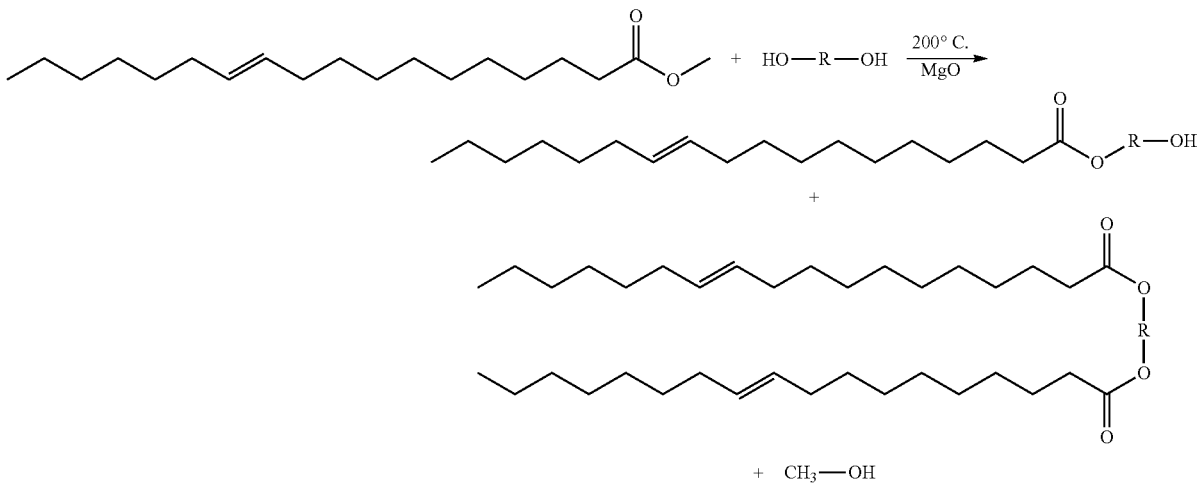

The prepared synthons (corresponding to the compounds of formula (IV)) are purified on a silica column for example with a 80:10:10 mixture of heptane/acetone/petroleum ether for the monoester and a 80:20 mixture of heptane/petroleum ether for the diester. The yields after purification are given in the table above.

At the end of this first step we have two precursors: the first is a monoester (compound of formula (IV-1)) having a terminal hydroxyl group and a double bond on the chain; the second is a diester (compound of formula (IV-2)) having exactly two double bonds for the subsequent obtaining of a symmetric polyol containing two hydroxyl groups. The synthesis route used is <<clean>> since it has recourse to heterogeneous catalysis (magnesium oxide) and the synthesis takes place solvent-free. For industrial purification, high vacuum distillation can be used.

2. Step b): Radical Addition Reaction of a Thiol on the Double Bond

To date there is no study dealing with the addition of a thiol onto monoesters or diesters previously transesterified with different diols. This novel route allows the obtaining of novel precursors having two primary alcohol functions.

Step b) (where $R_1=C_6H_{13}$; $A_1=C_9H_{18}$, $A_2$=ORO and $A_3=C_2H_4$) can be represented in particular by the following scheme:

$A_1$ is a divalent alkylene radical, straight-chain or branched, comprising 2 to 14 carbon atoms, $A_2$ is a radical —O-$A_4$-O—, $A_4$ representing a divalent alkylene radical, straight-chain or branched, comprising 1 to 20 carbon atoms, preferably 1 to 10 carbon atoms, optionally comprising one or more substituents chosen in particular from the group formed of the phenylene radical and the radical of formula —$(CH_2OCH_2)_n$—, n representing an integer of between 1 to 100, preferably 6 to 50 and it is preferably 6, 13 or 45, or $A_2$ is a radical of formula —$(OCH_2CH_2)_n$—O—, n being such as defined above, $A_4$ preferably representing a radical of formula —$CH_2$-$A'_3$-$CH_2$—, $A'_3$ representing a group of formula —$(CH_2OCH_2)_n$—, n representing an integer of between 1 to 100, preferably 6 to 50 and is 6, 13 or 45, or a phenylene radical,

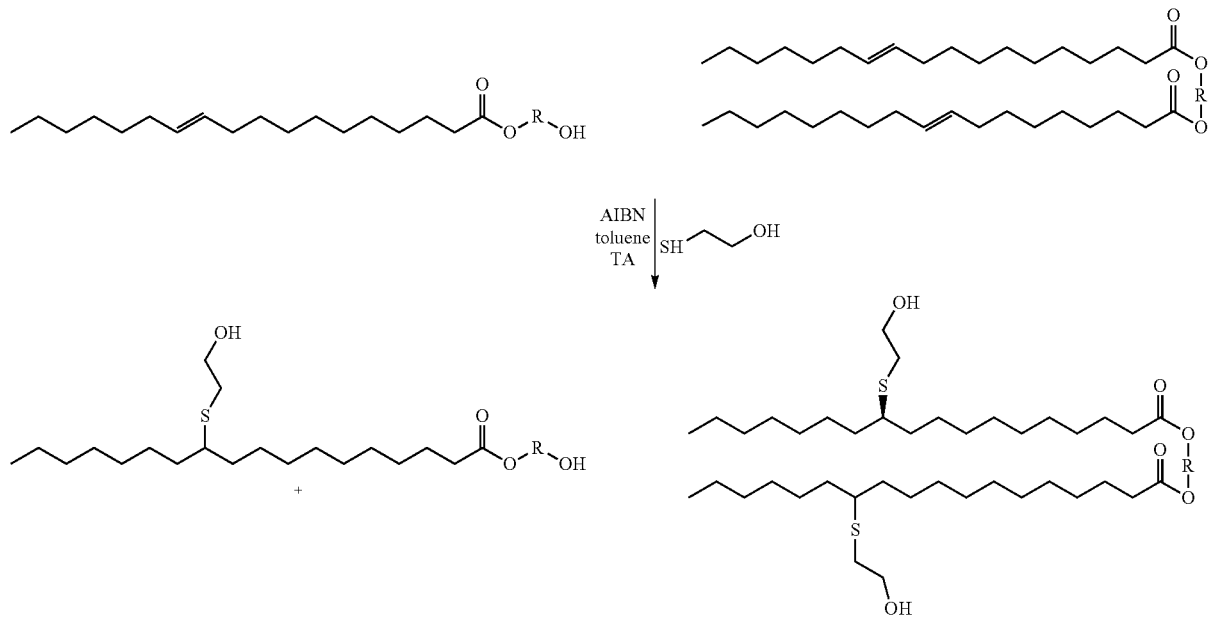

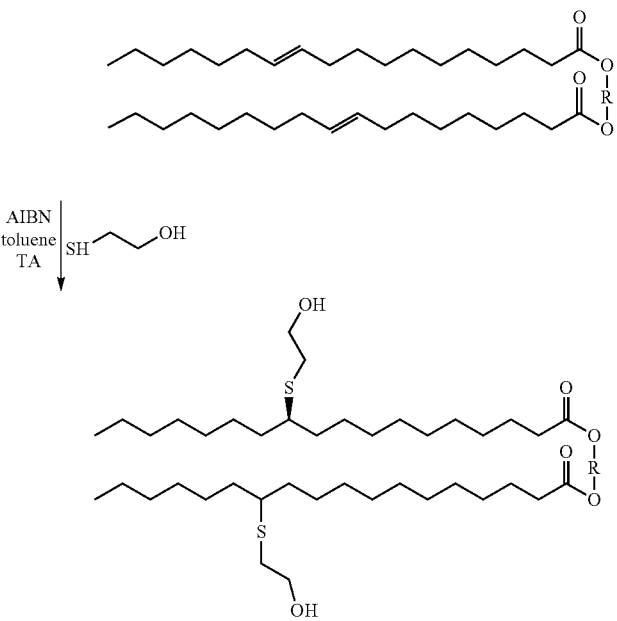

The synthons described above were prepared and purified on a silica column with a 60:40 mixture of toluene/ethyl acetate for the purification of the monoester and a 70:30 mixture for the diester.

The present invention also concerns compounds meeting the following general formula (I'):

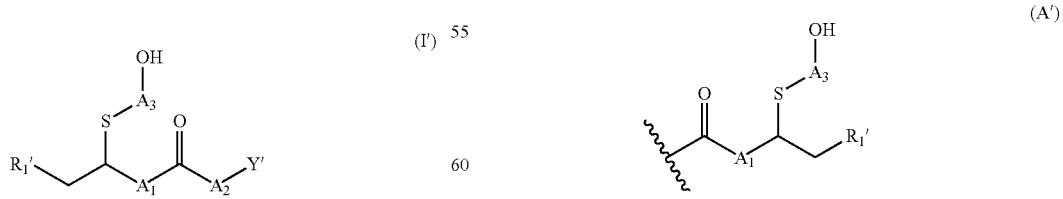

where:

$R'_1$ is a straight-chain or branched alkyl group comprising 1 to 14 carbon atoms, the said alkyl group optionally containing one or two side substituents —S-$A_3$-OH, $A_3$ is a divalent alkylene radical, straight-chain or branched, comprising 1 to 10 carbon atoms, optionally substituted, and Y' is a hydrogen atom or a group of formula (A')

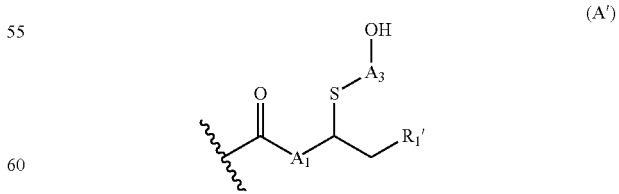

$A_1$, $A_3$ and $R'_1$ being such as defined above in formula (I').

The present invention also concerns compounds meeting the following general formula (I):

(I)

[Structure of formula (I): R₁–CH₂–CH(S–A₃–OH)–A₁–C(=O)–A₂–Y]

where:
R₁ is a straight-chain or branched alkyl group comprising 1 to 14 carbon atoms,
A₁, A₂ and A₃ are such as defined in formula (I') above, and
Y is a hydrogen atom or a group of formula (A)

(A)

[Structure of group (A)]

A₁, A₃ and R₁ being such as defined above.

Advantageous compounds of the invention are compounds meeting the following general formula (I-1):

(I-1)

[Structure of formula (I-1)]

where:
R₁, A₁, A₂, and A₃ are such as defined above in formula (I').

One family of preferred compounds of the invention is formed of compounds meeting the following general formula (I-1-1):

(I-1-1)

$H_3C\text{-}(CH_2)_p\text{-}CH(S\text{-}(CH_2)_q\text{-}OH)\text{-}(CH_2)_n\text{-}C(=O)\text{-}O\text{-}(CH_2)_m\text{-}OH$ where:
m, n, p and q are integers of between 1 and 18.

Another family of preferred compounds according to the invention is formed of compounds meeting the following general formula (I-1-2):

(I-1-2)

$H_3C\text{-}(CH_2)_5\text{-}CH(S\text{-}(CH_2)_2\text{-}OH)\text{-}(CH_2)_9\text{-}C(=O)\text{-}O\text{-}(CH_2)_m\text{-}OH$ Among the preferred compounds of the invention, particular mention may be made of the compounds meeting the following general formula (I-2):

(I-2)

[Structure of formula (I-2): dimeric diester structure]

where:
R₁, A₁, A₂ and A₃ are such as defined above.

Another family of preferred compounds of the invention is formed of compounds meeting the following general formula (I-2-1):

(I-2-1)

[Structure of formula (I-2-1)]

where:
m, n, p and q are integers of between 1 to 18.

Among the preferred compounds of the invention, particular mention can be made of the compounds of the following general formula (I-2-2):

(I-2-2)

[Structure of formula (I-2-2)]

The polyols of the present invention, the diols in particular, have the specificity of being well-defined with two primary hydroxyl groups. The diester derivatives are original on account of their symmetry and the alcohol used for transesterification allows the structure of the synthons to be varied and hence the properties of the resulting polymers.

The diols obtained with these different methods can then be used inter alia as monomers. Their purity allows optimization of the properties of the polymers obtained.

For example, polyurethanes were subsequently synthesized by mass polymerization of these polyols with IPDI (or for example also with MDI, HMDI or HDI), at 60° C. in the presence of tin dibutyl dilaurate. The formation of the polyurethanes was confirmed by FTIR with disappearance of the isocyanate vibration band. Size exclusion chromatography confirmed molar weights of between 14 000 and 50 000 g/mol. These di-OH monomers may also be used for the synthesis of other polymers such as polyesters, polyethers, polycarbonates, etc.

The polyol compounds of the present invention of formula (I) or (I') are particularly used for reaction with polyisocyanates.

Therefore these compounds can be used for preparing rigid foam, electrical insulation, coatings, adhesives, flexible foam (in particular in the furniture and automotive markets) or shoe soles.

More specifically, the polyols of the present invention are used for preparing rigid foam by causing them to react with polyisocyanates in the presence of a catalyst and a foaming agent (to which may also be added surfactants, dyes, antioxidants, preserving agents, plasticizers, cross-linking agents, flame-retardant agents, etc.).

Preferably, it is possible to prepare said rigid foam by causing to react all the following constituents: 60 g of polyisocyanate, 40 g of polyol, 1.2 g of water (foaming agent), 0.1-0.4 g of catalyst and 1-4 g of surfactant.

More specifically, the polyols of the present invention are used for preparing electrical insulation by causing them to react with polyisocyanates in the presence of an anti-foaming agent and a drying agent.

Preferably, said electric insulation can be prepared by reacting together 60 g of polyol, 29 g of polyisocyanate, 0.6 g of anti-foaming agent and 3 g of drying agent, and optionally 60 g of filler (silica).

More specifically, the polyols of the present invention are used for preparing coatings by causing them to react with polyisocyanates. For example, coatings are prepared using polyols and pure polyisocyanates, or using polyols and polyisocyanates with solvents (it is also possible to add dyes, pigments, fillers, rheological additives, anti-oxidants, bactericidals, fungicidals, corrosion inhibitors, catalysts or UV stabilizers).

For preparing adhesives according to the present invention, provision is also made for use of the polyols of the invention used pure with pure polyisocyanates.

Regarding flexible foam, preferable use is made of 60 g of polyol according to the invention, 100 g of isocyanate, 4.5 g of water (foaming agent), 0.12 g of catalyst 1, 0.38 g of catalyst 2, and 3 g of surfactant.

Finally, a specific formulation of the invention to prepare shoe soles comprises 59 g isocyanate, 94.5 g polyol according to the invention, 4.1 g of ethylene glycol and 1.4 g of catalyst.

EXPERIMENTAL PART

Example 1

Preparation of a diol of formula (I-2)

The protocol described below was used to synthesize compounds of formula (I-2), $A_1$ representing a radical $C_7H_{14}$, $A_3$ representing a radical $C_2H_4$ and $R_1$ representing an alkyl group comprising 9 carbon atoms.

In formula (I-2), $A_2$ may represent a radical chosen from among the following radicals: —$OC_3H_6O$—, —$OC_4H_8O$—, —$OC_6H_{10}O$—, —$OC_6H_{12}O$—, —$OH_2C$—$(CH_2OCH_2)_6$—$CH_2O$—, —$OH_2C$—$(CH_2OCH_2)_{13}$—$CH_2O$—, —$OH_2C$—$(CH_2OCH_2)_{45}$—$CH_2O$— or —$OH_2C$—$C_6H_4$—$CH_2O$—.

Transesterification Step:

The diesters are derived from the transesterification of an oleic methyl ester and a diol (propanediol, butanediol, pentanediol, hexanediol, poly(ethylene oxide) (300 g/mol, 600 g/mol and 2 000 g/mol)). Synthesis used 0.1 mol of oleic methyl ester and 0.05 mol of diol, in the presence of magnesium oxide MgO (catalyst, 1 weight % relative to the weight of the methyl ester). The medium was held under agitation at 160° C., in a stream of nitrogen, for 7 hours. The methanol formed by the reaction was removed from the reaction medium using a Dean Stark trap. The formation of the diester was monitored by $^1H$ NMR. After 7 h, the medium was placed at 200° C. under dynamic vacuum for 1 h to remove the oleic methyl ester and the residual diols. The catalyst was removed by filtration.

For the synthesis of the diester from a methyl ester and 1,4-benzenedimethanol ($A_2$=$H_2C$—$C_6H_4$—$CH_2$), the temperature of the medium at the time of the reaction was 140° C. so as not to sublimate the 1,4-benzenedimethanol.

Thiolation Step:

A mixture of 10 mmol of previously synthesized diester, 20 mmol of 2-mercaptoethanol (HS—$C_2H_4$—OH) and azobisisobutyronitrile (catalyst, 4 weight % relative to the weight of the diester) was dissolved in 3 ml of distilled toluene. The medium was heated to 70° C., under a stream of nitrogen for 8 h. The progress of the reaction was monitored by $^1H$ NMR. On completion of the reaction, the residual 2-mercaptoethanol was removed by distillation (180° C., under dynamic vacuum).

Example 2

Preparation of a Diol of Formula (I-1)

The protocol described below was used to synthesize compounds of formula (I-1), $A_1$ representing a radical $C_7H_{14}$, $A_3$ representing a $C_2H_4$ radical and R1 representing an alkyl group comprising 9 carbon atoms.

In formula (I-1), $A_2$ may represent a radical chosen from among the following radicals: —$OC_3H_6O$—, —$OC_4H_8O$—, —$OC_6H_{10}O$—, —$OC_6H_{12}O$—, —$OH_2C$—$(CH_2OCH_2)_6$—$CH_2O$—, —$OH_2C$—$(CH_2OCH_2)_{13}$—$CH_2O$—, —$OH_2C$—$(CH_2OCH_2)_{45}$—$CH_2O$— or —$OH_2C$—$C_6H_4$—$CH_2O$—.

The synthesis protocols are the same as those indicated for Example 1 with the exception of the transesterification step. Synthesis involved 0.1 mol of oleic methyl ester and 1.5 mol of diol, to promote the formation of monoesters in relation to the diesters.

Example 3

Preparation of Polymers from Polyols of Formula (I')

By applying the same procedure as in the aforementioned Examples 1 and 2, the following compound was synthesized:

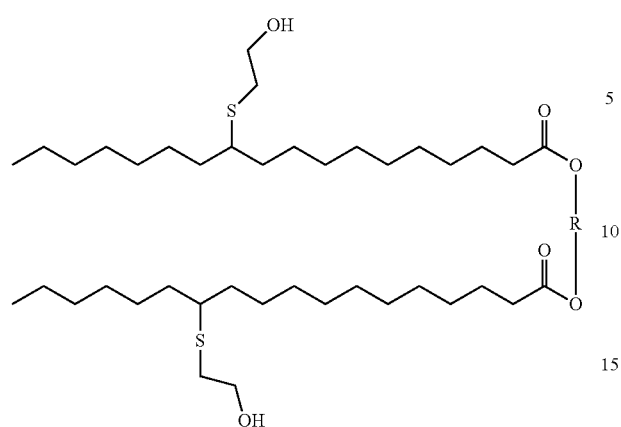

Synthesis of polymers derived from the polyol:

| R Group      | $C_3H_6$   |
| ------------ | ---------- |
| Reaction time | 1 h 30    |
| $M_w$        | 50 000 g/mol |
| IP           | 1.6        |

Example 4

Preparation of Diols of Formula (I-2)

The protocol described above in Example 1 was used for the synthesis of the following compounds:

the compound of formula (I-2), in which $A_1$ is a radical $C_8H_{16}$, $A_2$ is a radical —$OC_4H_8O$—I, $A_3$ is a $C_2H_4$ radical and $R_1$ is an alkyl group comprising 8 carbon atoms:

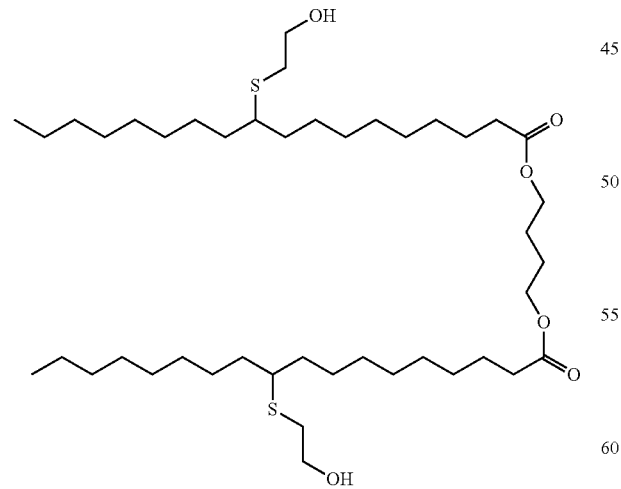

a compound of formula (I-2), where $A_1$ is a radical $C_8H_{16}$, $A_2$ is a radical —$(OCH_2CH_2)_{13}$—O—, $A_3$ is a radical $C_2H_4$, and $R_1$ is an alkyl group comprising 8 carbon atoms:

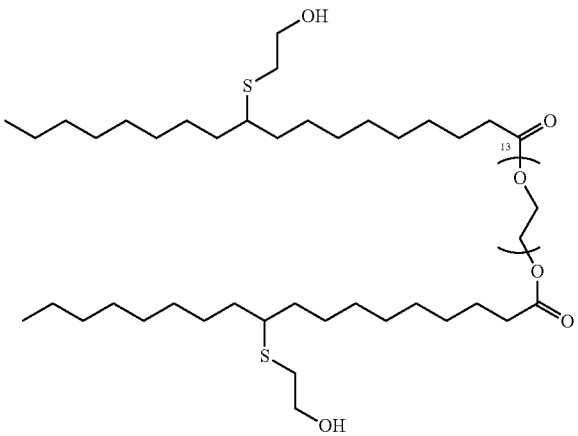

a compound of formula (I-2), where $A_1$ is a radical $C_8H_{16}$, $A_2$ is a radical —$(OCH_2CH_2)_{45}$—O—, $A_3$ is a radical $C_2H_4$ and $R_1$ is an alkyl group comprising 8 carbon atoms:

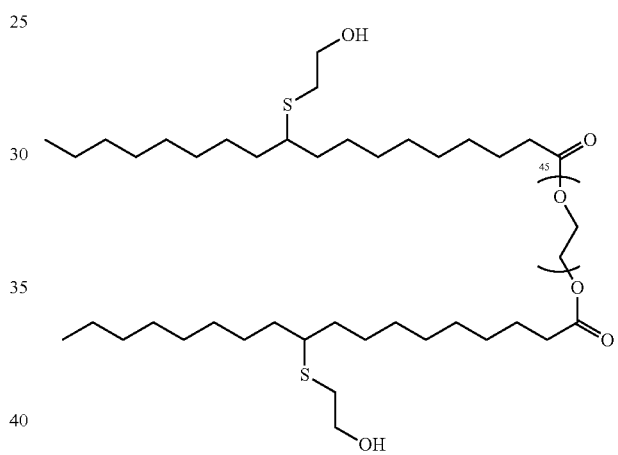

The invention claimed is:

1. A method for preparing a polyol meeting the following general formula (I'):

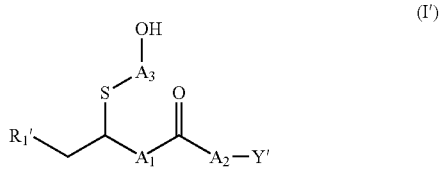

wherein:
$R'_1$ is a straight-chain or branched alkyl group comprising 1 to 14 carbon atoms, the said alkyl group optionally containing one or more side substituents —$S$-$A_3$-OH,
$A_i$ is a divalent alkylene radical, straight-chain or branched, comprising 2 to 14 carbon atoms,
$A_2$ is a —O-$A_4$-O— radical, $A_4$ is a divalent alkylene radical, straight-chain or branched, comprising 1 to 20 carbon atoms, optionally comprising one or more substituents, or $A_2$ is a radical of formula —$(OCH_2CH_2)_n$—O—, n representing an integer of between 1 to 100, $A_3$ is a divalent alkylene radical, straight-chain or branched, comprising 1 to 10 carbon atoms, optionally substituted, Y' is a hydrogen atom or a group of formula (A')

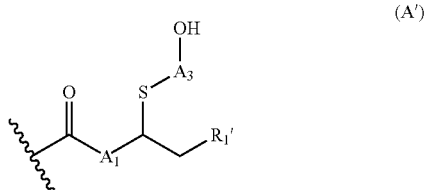

(A')

$A_1$, $A_3$ and $R'_1$ being such as defined above in formula (I'),
the said method comprising the following steps:
a) a transesterification step of a compound of following formula (II'):

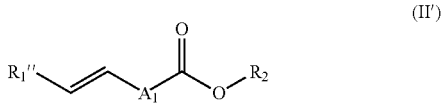

(II')

$A_l$ being such as defined above in formula (I'),
$R''_1$ representing a straight-chain or branched alkyl group comprising 1 to 14 carbon atoms, the said alkyl group optionally containing one or two double bonds, and
$R_2$ representing a straight-chain or branched alkyl group comprising 1 to 10 carbon atoms,
with a diol of following formula (III):

H-$A_2$-H (III)

$A_2$ being such as defined above in formula (I'),
to obtain a compound of following formula (IV'):

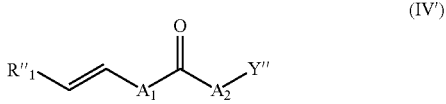

(IV')

$A_1$, $A_2$ and $R''_1$ being such as defined above, and,
Y'' representing a hydrogen atom or a group of formula (A'')

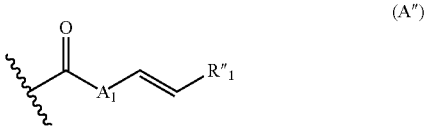

(A'')

$A_l$ and $R''_1$ being such as defined above,
b) a thiolation step of the compound of above-mentioned formula (IV') to obtain a compound of formula (I') such as defined above, and
c) a step to collect the compound of formula (I') such as defined above.

2. The method according to claim 1, wherein $A_4$ is a divalent alkylene radical, straight-chain or branched, comprising 1 to 10 carbon atoms.

3. The method according to claim 1, wherein n represents an integer of between 6 to 50.

4. The method according to claim 1, wherein n is 6, 13 or 45.

5. The method according to claim 1, wherein $A_4$ comprises one or more substituents chosen from the group formed of the phenylene radical and the radical of formula $(CH_2OCH_2)_n$—, n being as previously defined.

6. The method according to claim 1, wherein $R_2$ represents a straight-chain or branched alkyl group comprising 1 to 6 carbon atoms.

7. The method according to claim 1, to prepare a diol meeting the following general formula (I):

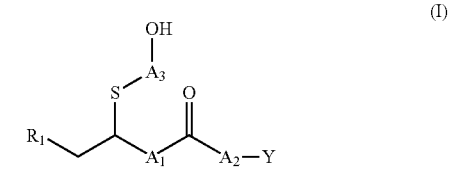

(I)

wherein: $R_1$ is a straight-chain or branched alkyl group comprising 1 to 14 carbon atoms,
$A_l$, $A_2$ and $A_3$ are as previously defined, and
Y is a hydrogen atom or a group of formula (A)

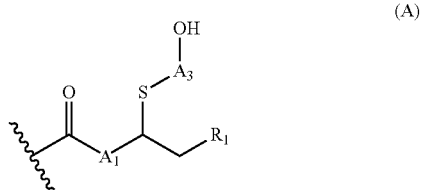

(A)

$A_l$, $A_3$ and $R_1$ being such as defined above,
the said method comprising the following steps:
a) a transesterification step of a compound of the following formula (II):

(II)

$R_1$ being such as defined above in formula (I),
$R_2$ and $A_l$ being as previously defined,
with a diol of following formula (III):

H-$A_2$-H (III)

to obtain a compound of compound of following formula (IV):

(IV)

$A_l$, $A_2$ and $R_1$ being such as defined above in formula (I), and $Y_1$ representing a hydrogen atom or a group of formula ($A_1$)

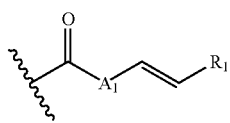
(A₁)

$A_1$ and $R_1$ being such as defined above, b) a thiolation step of the compound of above-mentioned formula (IV) to obtain a compound of formula (I) such as defined above, and c) a step to collect the compound of formula (I) such as defined above.

8. The method for preparing a diol according to claim 7, characterized in that the diol meets the following formula (I-1):

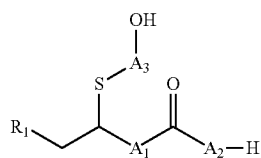
(I-1)

$A_1$, $A_2$, $A_3$ and $R_1$ being as previously defined.

9. The method for preparing a diol according to claim 7, characterized in that the diol meets the following formula (I-2):

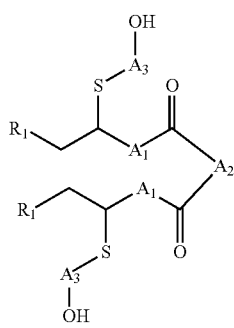
(I-2)

$A_1$, $A_2$, $A_3$ and $R_1$ being as previously defined.

10. The method for preparing a diol according to claim 1, wherein step a) is conducted in the presence of a catalyst chosen from the group formed of magnesium oxide, zinc acetate and sodium methanolate.

11. The method according to claim 10, wherein step a) is conducted at a temperature of between 150 and 200° C. under a stream of nitrogen.

12. The method for preparing a diol according to claim 1, wherein the thiolation step is a radical addition reaction in the presence of a radical initiator.

13. The method according to claim 12, wherein the radical initiator is azobisisobutyronitrile (AIBN).

14. The method according to claim 12, wherein the thiolation step is conducted in the presence of toluene at a temperature of between 60° C. and 80° C.

15. The method according to claim 14, wherein the temperature is of 70° C.

16. A compound meeting the following general formula (I'):

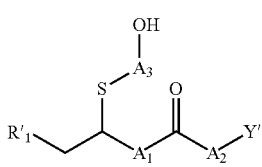
(I')

wherein:
$R'_1$ is a straight-chain or branched alkyl group, comprising 1 to 14 carbon atoms, the said alkyl group optionally containing one or two side substituents —S—$A_3$—OH, $A_1$ is a divalent straight-chain or branched alkylene radical, comprising 2 to 14 carbon atoms, $A_2$ is a radical —O-$A_4$-O—, $A_4$ representing a divalent alkylene radical, straight-chain or branched, comprising 1 to 20 carbon atoms, optionally comprising one or more substituents, or $A_2$ representing a radical of formula —(OCH$_2$CH$_1$)$_n$—O—, n representing an integer of between 1 and 100, $A_3$ is a divalent alkylene radical, straight-chain or branched, comprising 1 to 10 carbon atoms, optionally substituted, Y' is a hydrogen atom or a group of formula (A')

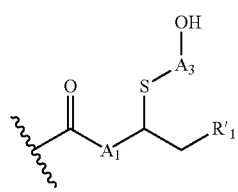
(A')

$A_1$, $A_3$ and $R'_1$ being such as defined above in formula (I').

17. The compound according to claim 16, wherein $A_4$ is a divalent alkylene radical, straight-chain or branched, comprising 1 to 10 carbon atoms.

18. The compound according to claim 16, wherein n represents an integer of between 6 to 50.

19. The compound according to claim 16, wherein n is 6, 13 or 45.

20. The compound according to claim 16, wherein $A_4$ comprises one or more substituents chosen from the group formed of the phenylene radical or the radical of formula —(CH$_2$OCH$_2$)$_n$—, n being as previously defined.

21. The compound according to claim 16 meeting the following general formula (I):

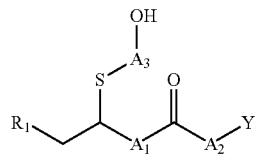
(I)

wherein:
$R_1$ is a straight-chain or branched alkyl group, comprising 1 to 14 carbon atoms,
$A_1$, $A_2$ and $A_3$ are as previously defined, and
Y is a hydrogen atom or a group of formula (A)

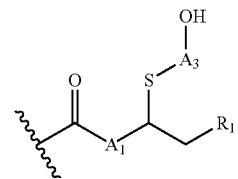
(A)

$A_1$, $A_3$ and $R_1$ being such as defined above.

22. The compound according to claim 21 meeting the following general formula (I-1):

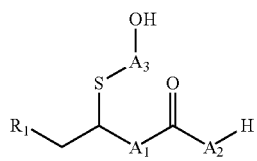
(I-1)

wherein:
$R_1, A_1, A_2,$ and $A_3$ are as previously defined.

23. The compound according to claim 21 meeting the following general formula (I-2):

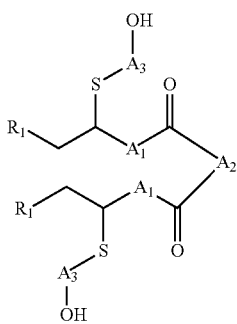
(I-2)

wherein:
$R_1, A_1, A_2$ and $A_3$ are as previously defined.

24. The compound according to claim 23 meeting the following general formula (1-2-1):

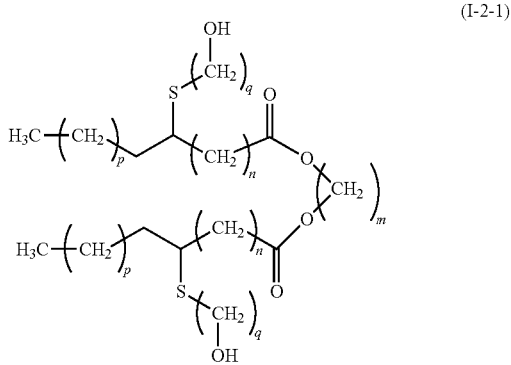
(I-2-1)

wherein:
m, n, p and q are integers of between 1 and 18.

* * * * *